United States Patent [19]

Shimizu et al.

[11] 4,365,081

[45] Dec. 21, 1982

[54] PROCESS FOR PRODUCING 2-HYDROXYALKYL ACRYLATES OR METHACRYLATES

[75] Inventors: Noboru Shimizu, Takatsuki; Hiroshi Yoshida, Toyonaka; Hiromiki Daigo, Minoo; Shiyouichi Matumoto, Ikeda; Hiroyoshi Uchino, Takatsuki, all of Japan

[73] Assignee: Nippon Shokubai Kagaku Kogyo Co. Ltd., Osaka, Japan

[21] Appl. No.: 263,935

[22] Filed: May 15, 1981

[30] Foreign Application Priority Data

| May 20, 1980 | [JP] | Japan | 55/65906 |
| May 20, 1980 | [JP] | Japan | 55/65907 |
| May 27, 1980 | [JP] | Japan | 55/69603 |
| Mar. 20, 1981 | [JP] | Japan | 56/39322 |

[51] Int. Cl.$^3$ ............... B01D 3/34; C07C 67/26; C07C 67/48
[52] U.S. Cl. .................. 560/209; 560/4; 560/218; 202/182; 202/185 A; 203/6; 203/8; 203/59; 203/61; 203/66; 203/DIG. 25
[58] Field of Search ............ 203/6, 8, 9, 38, 61, 203/66, 42, 49, 87, 95, 96, 59, DIG. 21, DIG. 25; 202/185 A, 182; 560/4, 209, 218

[56] References Cited

U.S. PATENT DOCUMENTS

| 2,996,351 | 8/1961 | Stöbe | 203/6 |
| 3,340,295 | 9/1967 | Wheeler et al. | 560/240 |
| 3,493,472 | 2/1970 | Schumacher | 203/42 |
| 3,725,208 | 4/1973 | Maezawa et al. | 203/8 |
| 3,852,160 | 12/1974 | Watson et al. | 203/6 |
| 3,954,566 | 5/1976 | Rajakovics | 202/185 A |
| 4,021,310 | 5/1977 | Shimuzu et al. | 203/8 |
| 4,069,242 | 1/1978 | Gurgiolo | 560/240 |
| 4,156,633 | 5/1979 | Horlenko et al. | 203/42 |
| 4,188,290 | 2/1980 | Graham et al. | 203/42 |
| 4,223,160 | 9/1980 | Hess | 560/240 |

*Primary Examiner*—Wilbur L. Bascomb, Jr.
*Attorney, Agent, or Firm*—Sherman & Shalloway

[57] ABSTRACT

In a process for producing a 2-hydroxyalkyl acrylate or methacrylate which comprises esterifying acrylic or methacrylic acid with an alkylene oxide having 2 to 4 carbon atoms in the presence of an esterification catalyst and distilling the resulting reaction mixture in a distillation column, the improvement wherein the vapor of the ester monomer from the distillation column, while being maintained in the superheated state, is introduced into a condenser of the gas-liquid direct contact type whose inner wall corresponding to its gas inlet portion is kept at a temperature below the boiling point of the ester at the operating pressure, to contact it directly with a concurrently flowing spray liquid of the ester-precooled to a temperature below the boiling point of the ester at the operating pressure, whereby said vapor is condensed to a liquid at said temperature below the boiling point of the ester at the operating pressure.

17 Claims, 1 Drawing Figure

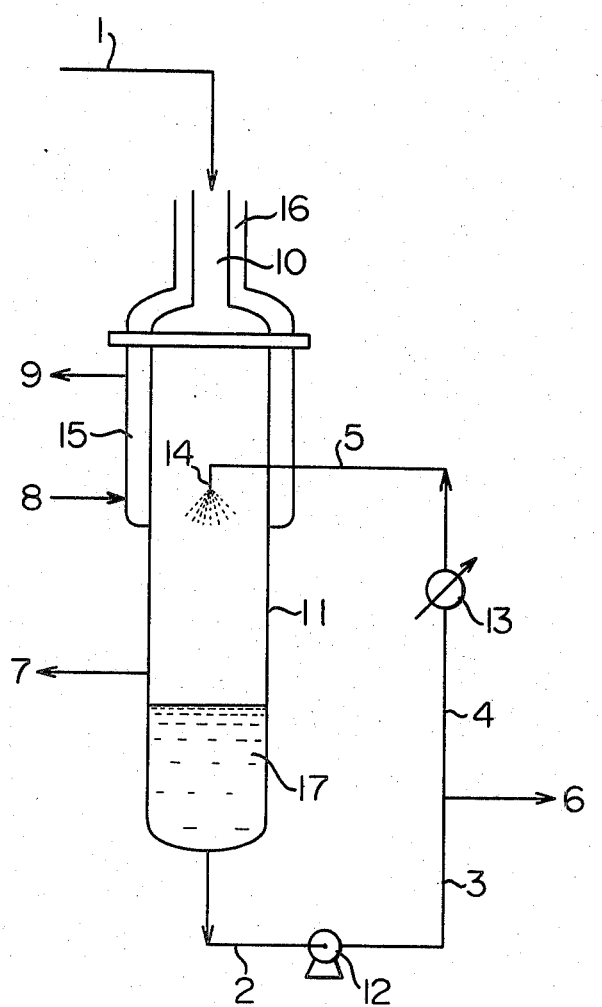

PROCESS FOR PRODUCING 2-HYDROXYALKYL ACRYLATES OR METHACRYLATES

This invention relates to a process for producing 2-hydroxyalkyl acrylates or methacrylates. More specifically, this invention relates to a process for producing a 2-hydroxyalkyl acrylate or methacrylate in a high yield which comprises esterifying acrylic or methacrylic acid and an alkylene oxide having 2 to 4 carbon atoms and distilling the reaction mixture to form the corresponding 2-hydroxyalkyl acrylate or methacrylate of high purity, characterized in that the vapor of the ester is condensed while inhibiting generation of a polymer of the ester; and to an industrial method for operating the above process in an industrial plant.

Heretofore, 2-hydroxyalkyl acrylates or methacrylates have been produced by esterification of acrylic or methacrylic acid with alkylene oxides. Various compounds have been suggested for use as a catalyst in this esterification reaction. These compounds include, for example, iron salts of organic acids such as iron acrylate or methacrylate, iron salts of inorganic acids such as ferric chloride, chromium compounds such as chromic acid, bichromic acid and ammonium bichromate, Lewis acids such as aluminum chloride, and organic bases such as tertiary amines or quaternary ammonium salts. Among the above compounds, the iron compounds have better activity and selectivity than the other compounds.

Ferric chloride, however, is disadvantageous for use in industrial operations because it will corrode the reaction apparatus or cause the coloration of the product and the formation of by-product chlorides.

In contrast, when the aforesaid esterification reaction is carried out by using as a catalyst a ferric salt of an organic carboxylic acid such as acrylic acid, methacrylic acid, benzoic acid, phthalic acid or salicylic acid, a 2-hydroxyalkyl acrylate or methacrylate free from coloration and having high quality and purity can be obtained with the reduced formation of an alkylene glycol diacrylate or dimethacrylate (to be abbreviated "diester").

The chromium compounds have good catalytic performance (activity and selectivity) although treatment of distillation bottoms containing chromium is difficult. Accordingly, like the iron compounds, they will quite possibly gain industrial acceptance.

In the aforesaid esterification reaction, it is the usual practice to use a polymerization inhibitor such as phenothiazines, hydroquinone, hydroquinone monomethyl ether and copper dialkyl dithiocarbamates. Thus, the esterification reaction is generally carried out in the presence of a catalyst and a polymerization inhibitor. The resulting reaction mixture contains not only the catalyst and polymerization inhibitor used but also some amounts of by-product high-boiling compounds. Evidently, therefore, it is difficult to use the reaction mixture directly as the desired 2-hydroxyalkyl acrylate or methacrylate, and it is industrially important to separate the ester from the reaction mixture and purify it with good efficiency.

A general method for separation and purification comprises distilling the reaction mixture under reduced pressure. However, since the ester has high polymerizability, no industrially advantageous method has been established previously for separating the ester from the reaction mixture by distillation while inhibiting its polymerization.

When the ester monomer is separated by distilling the esterification reaction mixture, the catalyst, the polymerization inhibitor and by-product high-boiling impurities are concentrated in the distillation still, and consequently, the viscosity of the reaction mixture in the still rises abruptly or it undergoes polymerization, thus making it difficult to distill off the ester in good yields. In particular, when an iron compound is used as the catalyst, the viscosity of the reaction mixture increases abruptly as the high-boiling compounds are concentrated in the still, until finally it is gelled. Thus, it is impossible to continue the distillation. As a result, the reaction mixture cannot be distilled in high yields. It has been desired therefore to develop an industrial process which permits separation of the ester from the reaction mixture in high yields and stably while inhibiting the increase of the viscosity of the reaction mixture being distilled, and which makes it possible to treat stably the distillation residue withdrawn from the still.

The present inventors made extensive investigations about an industrially advantageous process for distilling the reaction mixture to separate the ester without the trouble of polymerization and then condensing the vapor of the ester, and a process which permits condensing of the ester vapor stably while inhibiting the increase of the viscosity of the liquid in the distillation still. These investigations have led to the discovery of a number of interesting facts.

First, as regards the trouble of polymerization which may occur during the distillation of the esterification reaction mixture, it was found that the aforesaid monomer has very high polymerizability, and it is very difficult to separate and purify the ester while inhibiting the polymerization by the same methods as those applied to acrylic or methacrylic acid or to esters thereof with alcohols such as methanol or ethanol. When a large amount of a known polymerization inhibitor is used, polymerization of the ester within the distillation still can be prevented, but polymerization which occurs above and below the trays within the distillation column or at the gas inlet portion of the condenser can scarcely be inhibited. The polymerization at the condenser inlet or above or below the trays is due presumably to the condensation of the ester vapor. In an attempt to inhibit polymerization of this type, there was proposed a method which comprises performing distillation while adding a volatile polymerization inhibitor to the reaction mixture (see the specification of Japanese Laid-Open Patent Publication No. 78119/1973). Although this method may enable the polymerization within the distillation column and at the condenser to be inhibited, the inevitable inclusion of the volatile polymerization inhibitor in the distillate causes degradation of the quality of the final product. Hence, such a method cannot be employed industrially. Experimental work done in an attempt to elucidate the susceptibility of the ester to polymerization above and below the trays showed that even when a polymerization inhibitor (for example, 200 to 500 ppm of hydroquinone monomethyl ether) is included in the vapor of the ester, the ester polymerizes when the condensing temperature is high, and that the monomer liquid so condensed (containing 200 to 500 ppm of hydroquinone monomethyl ether) is liable to polymerize when it is evaporated at a temperature above its boiling point at the operating pressure. Accordingly, it was found that the provision of trays within the distillation column is not advantageous, and the distillation of the aforesaid ester must be done by a simple distillation method without trays, substantially by a flash distilling method, and in a passage from the distillation still to the condenser, the vapor of the ester should be superheated to prevent its condensation completely.

In regard to the polymerization of the ester in the condenser, it has been found that when an ordinary vertical-type multitube heat exchanger is used as the condenser, a polymer necessarily forms at the inlet portion of the heat exchanger. This is presumably because a part of the vapor condensed at the inlet portion, and before the liquefied monomer flows away, the vapor which newly comes into the condenser increases the temperature of the liquefied monomer. Thus, although it is advantageous to minimize the condensing temperature of the vapor, the reduction of the operating pressure to below 1 mmHg in an industrial apparatus is economically disadvantageous.

A spraying method using a cooling medium is conceivable in order to condense and trap the vaporous compound. It was found however that by merely contacting the superheated vapor of the ester monomer directly with a concurrently flowing spray liquid of the ester, the polymerization of the ester monomer cannot be completely prevented. This is presumably because the vapor of the monomer partly condenses on the inner wall of the condenser before its contact with the spray monomer liquid, and the condensed liquid is heated to a high temperature by the newly introduced vapor before it flows away. It was found however that the amount of a polymer formed at this time is much smaller than that formed in the case of using a vertical-type multitube condenser.

When a jacket is secured to the outer wall of the heat-exchanger of the gas-liquid direct contact type near its inlet portion, and the above process is carried out by heating the inner wall of the distillation column to a temperature above the condensing temperature of the monomer vapor and the spray liquid to a temperature above the condensing temperature of the monomer vapor, contacting the gas directly with the liquid, and rapidly cooling it at the lower portion of the heat exchanger, the polymerization of the monomer is reduced but cannot be completely inhibited. In this method, a part of the sprayed ester liquid evaporates on the inner wall and polymerization takes place at this portion.

The above findings can be summarized as follows:
(1) The condensed liquid of the ester does not easily polymerize if its re-evaporation is prevented.
(2) The vapor of the ester does not polymerize if its condensation is prevented.
(3) The vapor of the ester does not easily polymerize if its condensation is carried out at the lowest possible temperatures.
(4) The condensed liquid of the ester does not easily polymerize if it is rapidly cooled and rapidly caused to flow away.

The present inventors have investigated a process for condensation and trapping of 2-hydroxyalkyl acrylates or methacrylates which meets the above points (1) to (4), and discovered an effective process for condensing the ester vapor obtained by distillation of the esterification reaction mixture without the generation of polymerization.

This effective process for condensing the ester can be by itself used advantageously in industry, but the present inventors investigated it further in order to increase the yield of the ester in distillation. It was found that when a ferric salt of an organic acid is used as a catalyst in the esterification reaction, the distillation residue in the distillation of the esterification reaction mixture abruptly increases in viscosity as high-boiling components are concentrated particularly in the later stage of the distillation process, and it is gradually gelled to cause a failure of distillation, and that the yield of the ester in distillation is low and the yield of the product as a whole is restricted to a very low level. It was also discovered that when this distillation residue is taken out of the still and left to stand, popcorn polymerization takes place.

It has previously been considered due to the polymerization of the reaction mixture obtained by esterification of acrylic or methacrylic acid with an alkylene oxide to form the corresponding 2-hydroxyalkyl acrylate or methacrylate in the presence of an iron salt of an organic carboxylic acid as a catalyst that in the step of distilling the reaction mixture, the ratio of distillation increases and the viscosity of the distillation residue increases abruptly or the residue is gelled. The present inventors have surprisingly found that when a small amount of water or an organic acid such as acetic acid, propionic acid, acrylic acid or methacrylic acid is added to the gelled distillation residue, its gelled state disappears, and its viscosity abruptly decreases. This fact shows that the polymerization of the reaction mixture is not a cause of the viscosity increase or gellation of the distillation residue. The present inventors thus presumed that the viscosity rise and gellation of the distillation residue which occur in the distilling step are due not to the polymerization of the distillation residue but to the formation of a complex salt of the 2-hydroxyalkyl acrylate or methacrylate and the iron salt of the organic carboxylic acid used as the esterification catalyst.

Since the gradual increase of the distillation liquid with the progress of distillation makes it difficult to recover the ester in good yields, it is very important to establish a method for inhibiting formation of such a complex salt of the organic carboxylic acid iron salt.

The effect of the aforesaid compound to decompose the complex salt begins to be exhibited when the compound is caused to be present in the distillation liquid. Water or an organic acid such as acetic acid, propionic acid or acrylic acid or methacrylic acid is distilled as low-boiling fractions in the distillation step and cannot be present together with the liquid being distilled. Consequently, the effect of decomposing the complex salt is reduced, and the quality of the ester is reduced as a result of distillation of such a compound. According to this invention, acrylic or methacrylic acid is reacted with an alkylene oxide in the presence of a ferric salt of an organic carboxylic acid and without separating the catalyst, salicylic acid is added to the reaction mixture, after which the mixture is distilled. As a result, the viscosity increase of the liquid in the distillation still can be prevented and the difficulty in the distilling step can be overcome. By so doing, the distillation residue after distillation can be taken out in a low viscosity, and the subsequent treatment of the waste liquid can be performed easily. Thus, the deposition of scales to the heating section of the distillation still is prevented, and the distillation still can be maintained very easily. Thus, an industrially advantageous and safe manufacturing process has been provided.

With the progress of distillation, high-boiling compounds are concentrated in the distillation liquid and its viscosity increases greatly. Even when an iron compound is used as a catalyst and the distillation is not carried out in the presence of salicylic acid, 85 to 95% of the reaction product can usually be distilled out. However, the distillation residue having an increased viscosity is unstable after the distillation, and on standing, is liable to be gelled. The present inventors have extensively studied a method which comprises reducing the viscosity of the distillation residue which has been gelled or is about to be gelled, withdrawing the residue having a reduced viscosity, and treating it industrially safely and easily by burning, etc. to render it non-hazardous. As a result, they found a certain class of additive compounds which serve to decompose the iron-containing complex salt of complicated structure causing the viscosity increase and which do not induce polymerization of the ester monomer nor adversely affect the quality of the product.

Specifically, the inventors have found that when at least one compound selected from the group consisting of water, acetic acid, salicylic acid, ethanolamines and methanol is added to the distillation residue left after the distillation of the esterification reaction mixture obtained by reacting acrylic or methacrylic acid with an alkylene oxide having 2 to 4 carbon atoms in the presence of a ferric salt of an organic carboxylic acid, the viscosity of the distillation residue decreases, and even on standing outside the distillation system, the residue does not gel nor solidify but remains stable. By this method, the distillation residue can be withdrawn easily after the distillation, and since the residue can be maintained liquid, it can be easily burnt off or treated otherwise.

The troubles attributed to the polymerization of the ester in a condenser can be obviated by employing the condensing method in accordance with this invention for condensing the ester vapor obtained by the distilling operation. Furthermore, the co-presence of salicylic acid during the distillation inhibits the viscosity rise of the distillation liquid and makes it possible to stabilize the distillation residue and increase the ratio of distillation. Even when salicylic acid is not present during the distillation, the addition of at least one compound selected from water, acetic acid, salicylic acid, ethanolamines and methanol can reduce the viscosity of the distillation residue and stabilize it. By combining these methods, there can be provided a process for producing 2-hydroxyalkyl acrylates or methacrylates of high purity with commercial advantage in high overall yields without involving operational troubles by the esterification reaction of acrylic or methacrylic acid with alkylene oxides.

Investigations of the present inventors have also shown that when methacrylic acid is reacted with an alkylene oxide in the presence of a ferric salt of an organic carboxylic acid such as ferric methacrylate, the catalyst is degenerated and precipitates in the later stage of the reaction, and the rate of the reaction decreases abruptly so that for increasing the conversion of methacrylic acid, long periods of time and higher temperatures are required.

Such inconveniences for completing the reaction might further lead to undesirable side-reactions and to the reduced purity of the final product. Moreover, a large excess of the alkylene oxide must be fed in regard to methacrylic acid, and a step of recovering the unreacted alkylene oxide should be provided. Furthermore, the precipitated catalyst components will undesirably deposit on the reactor and the distillation still.

In order to overcome the aforesaid disadvantages in the esterification reaction of methacrylic acid and alkylene oxides in the presence of an iron salt of an organic carboxylic acid as a catalyst, the present invention provides an improved process for producing a 2-hydroxyalkyl methacrylate which comprises esterifying methacrylic acid and an alkylene oxide having 2 to 4 carbon atoms in the presence of an iron salt, particularly a ferric salt, of an organic carboxylic acid, characterized in that a solution of a catalyst obtained by dissolving the aforesaid iron salt in methacrylic acid is dehydrated and then used in the esterification reaction. According to this process, the decrease of the rate of the reaction in the later stage of the reaction is prevented and side-reactions can be inhibited to give a product of high purity and high quality. Moreover, the amount of the alkylene oxide fed can be made almost quantitative with respect to methacrylic acid and thereby the step of recovering the alkylene oxide can be rendered substantially unnecessary. Another advantage is that the deposition of the catalyst material is inhibited and scale formation on the reactor or the distillation still can be substantially obviated.

The present inventors have found that it is due to the presence of water in the reaction mixture that the catalyst tends to precipitate in the later stage of the reaction of methacrylic acid and the alkylene oxide to form a 2-hydroxyalkyl methacrylate and the rate of the reaction abruptly decreases. In other words, the degree of precipitation of the catalyst material is greatly affected by the amount of water in the reaction mixture. Generally, the iron salt of an organic carboxylic acid used in the process of this invention is prepared before it is used in the esterification reaction. It is always prepared as a basic salt or an iron compound containing water of crystallization. Furthermore, because the catalyst solution is prepared by dissolving iron powder in the starting methacrylic acid while blowing molecular oxygen into it, water is formed in the course of forming ferric methacrylate. It is presumed that water inevitably included in the reaction mixture will cause formation of an iron compound difficultly soluble in the resulting ester in the later stage of the esterification reaction. This phenomenon is scarcely observed in the case of esterifying acrylic acid. Accordingly, such an operating method in accordance with this invention is also applicable to the esterification of acrylic acid.

It will be economically advantageous to use the ferric salt of an organic carboxylic acid in the form of a solution of the ferric salt in acrylic or methacrylic acid prepared by dissolving iron powder in acrylic or methacrylic acid while blowing a molecular oxygen-containing gas and if desired, dehydrating the resulting solution.

In one embodiment of the process of this invention, wherein a 2-hydroxyalkyl acrylate or methacrylate is obtained by distilling the reaction mixture obtained by the reaction of acrylic or methacrylic acid with an alkylene oxide, an empty column is used as a distillation column; the monomer vapor leaving the still is introduced in the superheated state into the condenser by heating the outer wall of the conduit pipe or the column; the condenser is of the gas-liquid concurrent direct-contact heat exchange type; the inner wall of the condenser at the inlet of the monomer vapor is externally cooled to a temperature below the boiling point of the ester, preferably to a temperature 10° C. below the boiling point, especially preferably to a temperature 20° C. below the boiling point to room temperature; the ester liquid pre-cooled to below the boiling point of the ester at the operating pressure, preferably to 10° C. below the boiling point, especially preferably to 20° C. below the boiling point to room temperature is sprayed onto the monomer vapor; and the superheated vapor introduced is condensed at a temperature below the boiling point at the operating pressure, preferably at a temperature 10° C. below the boiling point, especially preferably at a temperature 20° C. below the boiling point to room temperature. According to such a purifying method for the 2-hydroxyalkyl acrylate or methacrylate, high-purity 2-hydroxyalkyl acrylates or methacrylates can be obtained with industrial advantage from the reaction mixture of acrylic or methacrylic acid and the alkylene oxide without any troubles attributed to the polymerization of the ester. Since the 2-hydroxyethyl acrylate has high polymerizability and high toxicity causing skin troubles, etc., the removal of troubles caused by the polymerization is very effective in performing industrial production of 2-hydroxyethyl acrylate.

The characteristic of the present invention is that the condensation of the vapor is carried out at a temperature below the boiling point of the ester at the operating pressure, and a greater portion of the monomer vapor is condensed by direct contact with the spray liquid flowing concurrently, and even when the vapor is partly condensed, the remainder can be rapidly cooled to a low temperature. According to the process of this invention, not only 2-hydroxyethyl acrylate, but also 2-hydroxyethyl methacrylate and 2-hydroxypropyl acrylate or methacrylate can be obtained as a highly pure monomer without the formation of a polymer.

Accordingly, the 2-hydroxyalkyl acrylates or methacrylate intended in the present invention are not limited to the above-exemplified monomeric compounds, but include esters obtained by the esterification of acrylic or methacrylic acid and alkylene oxides having 2 to 4 carbon atoms. The esterification reaction product is purified and separated by the distillation operation described hereinabove.

The distillation column employed in the present invention is an empty column. The column or a conduit pipe must be heated by steam or a heat transfer medium by providing a jacket therearound. The superheating temperature is higher than the boiling point of the vapor at the operating pressure, preferably 10°–50° C. higher than the boiling point. To prevent mists from forming during evaporation, it is desirable to provide a demister (e.g., a wire mesh) in the column. Of course, to prevent condensation of the vapor on the demister, the demister must be provided at a superheated state. The operating pressure should desirably be adjusted so that the distilling temperature is not more than 120° C., preferably in the range of 60° to 100° C.

The condenser is of a vertical structure which permits the monomer vapor introduced and the pre-cooled spray liquid of the monomer to be contacted as concurrent flows. It is necessary that the inner wall of the upper portion of the condenser at which the vapor of the introduced monomer contacts the spray liquid should be externally cooled so that it can be kept at a temperature below the boiling point of the ester, preferably 10° C. below the boiling point, especially preferably a temperature 20° C. below the boiling point to room temperature. Preferably, a jacket is provided externally and cooling water or a cooling medium is circulated through it. Furthermore, the surface of the inner wall should preferably be smooth without unevenness so that the liquefied monomer can rapidly flow away.

The suitable proportion of the spray liquid is 10 to 200 times the weight of the vapor. If it is too small, sufficient contacting may not take place and polymerization will occur. The temperature of the spray liquid is below the boiling point of the ester, preferably 10° C. below the boiling point, especially preferably 20° C. below the boiling point to room temperature. When the diameter of the column is large and the amount of the spray liquid is large, a plurality of spray nozzles can suitably be used. The liquid to be sprayed is the monomer liquid which is the final product. It contains a polymerization inhibitor corresponding to the quality of the product, preferably hydroquinone monomethyl ether. The circulating spray liquid is cooled to a predetermined temperature by an external cooler, for example by cooling water. The operating temperature of the condenser is below the boiling point of the ester at the operating pressure, preferably 10° C. below the condensation temperature of the monomer vapor, especially preferably 20° C. below the boiling point to room temperature. It is not necessary to cool it to below room temperature, or to below 0° C.

The process of the invention is illustrated with reference to the accompanying drawing which is a diagrammatical scheme for explaining a preferred embodiment of the present invention.

A vapor of a 2-hydroxyalkyl acrylate or methacrylate coming from a distillation still (not shown) is heated with steam by a jacket (not shown) of the distillation column and a jacket 16 of a conduit 10, and in the superheated state, comes into the upper portion of a condenser 11 through a line 1. At the inlet portion of the condenser 11, a jacket 15 is provided at the outer wall of the condenser. Cooling water is caused to flow from a line 8 to cool the inner wall and the cooling water is discharged through a line 9. The vapor which has entered the condenser 11 contacts concurrently with droplets of the precooled ester liquid introduced from a line 5 and sprayed by a spray nozzle 14, whereby it is cooled and condensed and gathers at the bottom of the condenser 11.

The ester liquid which gathers at the bottom of the condenser is drawn into a line 3 through a line 2 by means of a pump 12. A greater portion of the ester liquid is cooled to a predetermined temperature at an external cooler 13 through a line 4, and circulated to the spray nozzle 14 through a line 5. The condensed ester as a product is withdrawn from a line 6. A line 7 is an exhaust line which is connected to a vacuum pump (not shown) through an after cooler (not shown) so as to maintain the distillation system under a predetermined reduced pressure.

Salicylic acid which is added in the present invention to the reaction mixture so as to inhibit the viscosity rise of the distillation liquid during the distillation and increase the ratio of distillation and stabilize the distillation residue is 0.05 to 10% by weight, preferably 0.1 to 5% by weight, based on the reaction mixture before distillation. Salicylic acid may be added to the reaction mixture directly in the form of crystals after the esterification reaction, or in the form of a solution in the reaction mixture or in a small amount of the ester. Or it may be added at a time when the viscosity rise is likely to occur during the distillation of the reaction mixture. The method and time of addition of salicylic acid are not critical, however.

The reaction mixture obtained by the esterification reaction is subjected to flash distillation at 50° to 120° C. and 1 to 10 mmHg after adding salicylic acid. Preferably, the unreacted alkylene oxide is removed as an initial distillate under reduced pressure.

Examples of the alkylene oxide having 2 to 4 carbon atoms used in this invention are ethylene oxide, propylene oxide and butylene oxide. The amount of the alkylene oxide used is at least 1 mole, preferably 1.05 to 1.2 moles, per mole of the acrylic or methacrylic acid.

Examples of the ferric salts of organic carboxylic acids used in this invention include ferric salts of aliphatic unsaturated carboxylic acids such as acrylic acid or methacrylic acid, and ferric salts of aromatic carboxylic acids such as phthalic acids (e.g., orthophthalic acid and metaphthalic acid), and salicylic acid. A solution of iron powder in the starting acrylic or methacrylic acid can also be used. The amount of the catalyst is 0.1 to 5 mole%, preferably 0.5 to 2 mole%, based on the starting acrylic or methacrylic acid. The co-presence of the ferric salt and a ferrous salt does not adversely affect the process of the invention.

In the esterification step or the purifying distillation step, p-methoxyphenol, hydroquinone, phenothiazines, tannic acid and copper dialkyldithiocarbamates (the alkyl group has 1 to 4 carbon atoms), which are usually employed as polymerization inhibitors, are added. The amount of the polymerization inhibitor is 0.01 to 5% by weight based on acrylic or methacrylic acid. Preferably, at least one of p-methoxyphenol, hydroquinone, phenothiazines and copper diethyl- and dibutyl-dithiocarbamate is used. It has been found that the presence of 0.01 to 5% by weight, based on the reaction mixture, of a copper dialkylthiocarbamate in the reaction mixture being distilled is favorable for preventing the viscosity rise and polymerization of the distillation liquid. It has also been found that in the distillation step, a better polymerization inhibiting effect can be obtained by performing the distillation while passing a molecular oxygen-containing gas in an amount of 0.05 to 2.0% by volume based on the volume of the vapor into the distillation column.

In an embodiment in which the viscosity of the distillation residue is reduced to stabilize it, the esterification reaction is carried out under the same conditions as described above with regard to the process involving distilling the reaction mixture in the presence of salicylic acid, the reaction mixture is distilled under the same conditions except that salicylic acid is not caused to exist together, and after the distillation, an additive is added to the distillation residue. Specifically, after the esterification reaction, the reaction mixture is distilled at a temperature of 50° to 120° C., preferably 60° to 100° C., under a pressure of 1 to 10 mmHg, preferably 2 to 5 mmHg, to distill off the 2-hydroxyalkyl acrylate or methacrylate until the distillation residue is about to be gelled. Then, at least one additive selected from the group consisting of water, acetic acid, salicylic acid, ethanolamines, and methanol is gradually added in an amount of 0.5 to 30% by weight, preferably 1 to 20% by weight, to the distillation residue. The mixture is stirred and withdrawn from the distillation still. Of course, the distillation residue may be withdrawn from the distillation still immediately after the distillation, and the additive may be added in to the residue in a separate receptacle.

The distillation residue to which the additive has been added is a flammable flowing mass containing some amount of the 2-hydroxyalkyl acrylate or methacrylate, and can be effectively used directly as a fuel.

In another embodiment in which methacrylic acid is reacted with the alkylene oxide at an increased rate of reaction, a solution of the ferric salt of an organic carboxylic acid as an esterification catalyst in the reaction mixture, particularly methacrylic acid is prepared, and the solution is distilled under atmospheric or reduced pressure to remove a part of the methacrylic acid as an azeotrope with water. Or an entrainer such as benzene, toluene, or methyl isobutyl ketone is added to the reaction solution, and water is distilled off as an azeotrope with such an entrainer. In this way, the water content of the solution should be adjusted to not more than 0.1% by weight, preferably to not more than 0.08% by weight. The distilled methacrylic acid or the entrainer containing water is re-used after separating water. To remove water from the above solution, a procedure of adding a water adsorbent such as molecular sieves or anhydrous sodium sulfate, or a procedure of passing the solution through a column of such a water adsorbent is recommended. The dehydrating operation, however, is not limited to these procedures alone, and all methods which can be applied to the process of this invention are used.

When the solution of the catalyst in the reaction mixture, especially methacrylic acid, is dehydrated and then heated to the reaction temperature of 40° to 120° C. with stirring and an alkylene oxide having 2 to 4 carbon atoms in the liquid or gaseous state is fed at atmospheric pressure, the reaction immediately proceeds.

In an embodiment in which iron powder is dissolved in acrylic or methacrylic acid, the iron powder used has such a particle diameter that it is dispersed in an organic carboxylic acid with stirring. Usually, it has a particle diameter of 50 to 500 mesh. The molecular oxygen-containing gas to be passed may be air which is used either as such or as diluted with an inert gas such as nitrogen. Air having an increased oxygen concentration (so-called enriched air) may also be used. Conveniently, air is directly used. The suitable amount of the air is about 1.5 to 2.0 liters/g of iron powder/hour.

During the dissolving of the iron powder, 0.05 to 1.0% by weight, based on acrylic or methacrylic acid, of a polymerization inhibitor such as methoxyhydroquinone, hydroquinone, phenothiazines, or a sodium, potassium or copper salt of a dialkyldithiocarbamic acid (the alkyl group having 1 to 4 carbon atoms) is included.

The dissolving operation is completed in 50 to 100 minutes at a temperature of 30° to 150° C., preferably 50° to 120° C. A temperature of 150° C. is a maximum applicable temperature because acrylic or methacrylic acid is likely to polymerize even in the presence of a polymerization inhibitor when exposed to high temperatures for a long period of time.

The following Examples and Comparative Examples illustrate the present invention more specifically. It is to be understood that the invention is in no way limited to these specific examples.

EXAMPLE 1

A 200-liter reactor (made of SUS 316 stainless steel) equipped with a refluxing device, a thermometer, a heating device, a cooling device and a stirrer was charged with 100 kg of acrylic acid, 240 g of p-methoxyphenol and 150 g of copper dibutyldithiocarbamate, and then as a catalyst, 2.9 kg of ferric acrylate was added. The reactor was heated to 70 C., and while maintaining this temperature, 64.5 kg of ethylene oxide was added over 3 hours. After the addition of ethylene oxide, the mixture was further maintained at 70° C. for 2 hours to complete the reaction. The reaction mixture was cooled.

Forty liters of the resulting reaction mixture was put in a stainless steel distillation still having a capacity of 70 liters, and then 40 g of copper dibutyldithiocarbamate was added to the mixture. The mixture was distilled as shown in the accompanying flowsheet. A jacket was secured to the bottom of the distillation still and the reaction mixture was heated with steam to evaporate it. The operating pressure in the distillation was 3 mmHg, and the temperature of the still was 70° to 85° C. The distillation time was 4 hours, and the distillation was performed while introducing air into the reactor at a rate of 21 liters/hour. Thus, 35 liters of the condensed liquid was obtained. This product had a purity of 97%.

The distillation column was an empty column made of a stainless steel and having an inside diameter of 150 mm, a stainless steel wire mesh was put in the column to a height of 100 mm to use it as a demister. Steam under a pressure of 2 kg/cm$^2$.G was passed through jackets secured to the column and the conduit. The condenser was made of stainless steel and had an inside diameter of 200 mm and a height of 3,000 mm. At the upper part of the condenser, a jacket was provided which extended downwardly from its top to a point corresponding to one third of the height of the condenser. Cooling water at 25° C. was caused to flow through the jacket. The temperature of the spray liquid was adjusted to 50° C., and the amount of the spray liquid sprayed was 1,000 liters per hour. The spray liquid contained 250 ppm of hydroquinone monomethyl ether. The temperature of the liquid at the bottom of the condenser was 51° C.

After the distillation, the insides of the still, column and condenser were inspected, but no polymer was seen to be deposited.

EXAMPLE 2

Using the same reactor as used in Example 1, 100 kg of methacrylic acid, 240 g of p-methoxyphenol and 150 g of copper dibutyldithiocarbamate were added, and 3.7 kg of ferric benzoate was added as a catalyst. The reactor was heated to 80° C., and while maintaining the reactor at this temperature, 53.7 kg of ethylene oxide was added over the course of 4 hours. After the addition of ethylene oxide, the mixture was further maintained at 80° C. for 3 hours to complete the reaction. The reaction mixture was cooled.

Forty grams of copper dibutyldithiocarbamate was further added to 40 liters of the resulting reaction mixture, and the mixture was distilled under the same conditions as in Example 1 except that the temperature of the distillation still was kept at 73° to 88° C. The product had a purity of 97.5%.

After the distillation, the insides of the still, column and condenser were inspected, but no polymer was seen to be deposited.

COMPARATIVE EXAMPLE 1

Forty grams of copper dibutyldithiocarbamate was added to 40 liters of the reaction mixture obtained in Example 1, and the mixture was distilled in the same apparatus as used in Example 1. During the distillation, hot water at 80° C. was circulated through the jacket of the condenser, and the temperature of the spray liquid was adjusted to 80° C. so that condensation of the vapor in the upper portion of the condenser was prevented. After 4 hours' distillation, about 150 g of the polymer deposited on the inner wall of the upper portion of the condenser.

COMPARATIVE EXAMPLE 2

Forty grams of copper dibutyldithiocarbamate was added to 40 liters of the reaction mixture obtained in Example 1, and the mixture was distilled in the same apparatus as in Example 1. During the distillation, no material was circulated through the upper jacket of the condenser, but the atmospheric air was let therein. After 4 hours' distillation, about 50 g of the polymer deposited on the inner wall of the upper portion of the condenser.

COMPARATIVE EXAMPLE 3

A vertical multitube heat exchanger consisting of ten stainless steel tubes having an inside diameter of 25 mm and a length of 1,000 mm was used as a condenser. While circulating cool water at 25° C. through it, the same distillation as in Example 1 was performed using the same distillation still, column and conduit. After 4 hours' distillation, the condenser was inspected, and it was found that a large amount of the polymer deposited on the upper portion of the heat-transmitting pipe of the condenser.

EXAMPLE 3

A 200-liter reactor (made of SUS 316 stainless steel) equipped with a refluxing device, a thermometer, a heating device, a cooling device and a stirrer was charged with 100 kg of acrylic acid, 240 g of p-methoxyphenol, 150 g of copper dibutyldithiocarbamate, and as a catalyst, 2.0 kg of ferric acrylate was added. The reactor was maintained at 70° C., and 64.5 kg of ethylene oxide was gradually added over 3 hours. After the addition of ethylene oxide, the mixture was maintained at 70° C. for 2 hours to complete the reaction. The reaction mixture was cooled.

The amount of the unreacted acrylic acid in the reaction mixture was 0.7% by weight. Salicylic acid (120 g) and 50 g of copper dibutyldithiocarbamate were added to one-third of the resulting reaction mixture, and the mixture was distilled in a flash distillation apparatus (diameter 150 mm, height 1500 mm) at about 70° to 80° C. and 3 mmHg while passing oxygen into the distillation column in an amount of about 0.2 to 0.3% by volume based on the amount of the vapor. There was obtained 52 kg of a product.

The distillation residue in the still had a viscosity of 80 cps at 70° C., and 300 cps at room temperature.

COMPARATIVE EXAMPLE 4

The same flash distillation as in Example 3 was carried out except that 50 g of copper dibutyldithiocarbamate was added to one-third of the reaction mixture obtained in Example 3, and salicylic acid was not added. There was obtained 46.7 kg of a product. After the distillation, the residue in the still had a viscosity of 295 cps at 70° C., and solidified at room temperature.

COMPARATIVE EXAMPLE 5

One-third of the reaction mixture obtained in Example 3 was subjected to the same flash distillation as in Example 3 without adding any additive. When about 60% of the ester distilled, the viscosity of the mixture in the still increased, and further distillation failed.

EXAMPLE 4

The same reactor as used in Example 3 was charged with 100 kg of methacrylic acid, 240 g of p-methoxyphenol and 150 g of copper dibutyldithiocarbamate, and 3.7 kg of ferric benzoate was added. Then, the reactor was heated to 80° C., and while maintaining the reactor at this temperature, 53.7 kg of ethylene oxide was added over 4 hours. After the addition of ethylene oxide, the mixture was further maintained at 80° C. for 3 hours to complete the reaction. The reaction mixture was cooled.

The amount of the unreacted methacrylic acid in the reaction mixture was 1.0% by weight. Salicylic acid (170 g) and 75 g of copper dibutyldithiocarbamate were added to one half of the reaction mixture, and the mixture was subjected to flash distillation in the same way as in Example 3 to give 72 kg of a product. After the distillation, the residue in the still had a viscosity of 60 cps at 70° C., and 280 cps at room temperature.

COMPARATIVE EXAMPLE 6

To one half of the reaction mixture obtained in Example 4 was added 75 g of copper dibutyldithiocarbamate, and without adding salicylic acid, the mixture was subjected to flash distillation in the same way as in Example 3. There was obtained 64 kg of a product. After the distillation, the residue in the still had a viscosity of 90 cps at 70° C. and solidified at room temperature.

EXAMPLE 5

The same reaction as in Example 3 was carried out except that 84.3 kg of propylene oxide was used instead of the ethylene oxide and the reaction temperature was changed to 80° C. The amount of the unreacted acrylic acid in the resulting reaction mixture was 0.8% by weight. Salicylic acid (180 g) and 75 g of copper dibutyldithiocarbamate were added to one half of the resulting reaction mixture, and the mixture was subjected to flash distillation in the same way as in Example 3 to give 87.5 kg of a product. After the distillation, the residue in the still had a viscosity of 85 cps at 70° C. and 350 cps at room temperature.

COMPARATIVE EXAMPLE 7

To one half of the reaction mixture obtained in Example 5 was added 75 g of copper dibutyldithiocarbamate, and without adding salicylic acid, the mixture was subjected to flash distillation in the same way as in Example 3 to give 78 kg of a product. After the distillation, the residue in the still had a viscosity of 360 cps at 70° C. and solidified at room temperature.

EXAMPLE 6

Acrylic acid (216 g) was taken into a 500 cc three-necked glass flask equipped with a refluxing device and a stirrer, and 0.2 g of copper dibutyldithiocarbamate was added at room temperature and dissolved in the acrylic acid. To the resulting solution was added 1.3 g of iron powder, and the mixture was heated to 70° C. while passing air to dissolve the iron powder. Then, while cooling the flask externally with warm water so that the temperature of the reaction system did not exceed 70° C., 158 g of ethylene oxide in gaseous state was blown into the flask over 3 hours. The ethylene oxide condensed in the refluxing device was not returned to the reaction system but was recovered out of the reaction system. The amount of the ethylene oxide recovered was 6.5 g. After blowing the ethylene oxide, the mixture was maintained at 70° C. for 2 hours to complete the reaction. The reaction mixture was cooled. The amount of the unreacted acrylic acid in the reaction mixture was 0.5% by weight. To the resulting reaction mixture were added 0.8 g of salicyclic acid and 0.4 g of copper dibutyldithiocarbamate, and the mixture was subjected to simple distillation at about 70° to 80° C. and 3 mmHg while passing oxygen into the distillation column in an amount of about 0.2 to 0.3% by volume based on the volume of the vapor. After the distillation, the residue in the still had a viscosity of 85 cps at 70° C., and 345 cps at room temperature.

EXAMPLES 7 TO 10 AND COMPARATIVE EXAMPLES 8 AND 9

A 200-liter stainless steel reactor equipped with a refluxing device, a thermometer, a heating device, a cooling device and a stirrer was charged with 100 kg of acrylic acid, 240 g of p-methoxyphenol and 150 g of copper dibutyldithiocarbamate. Then, 600 g of iron powder was added, and the mixture was heated to 70° C. while passing air, thereby dissolving the iron powder. After sealing the reactor, 64.5 kg of liquid ethylene oxide was added over 3 hours while the inside of the reactor was maintained at 70° C. After the addition of ethylene oxide, the mixture was maintained at 70° C. for 2 hours to complete the reaction. The reaction mixture was cooled to room temperature.

The amount of the unreacted acrylic acid in the reaction mixture was 0.7% by weight. To ¾ of the reaction mixture was added 124 g of copper dibutyldithiocarbamate, and the mixture was distilled in a flash distillation device (150 mm in diameter, 1500 mm in height) at about 70° to 80° C. and 3 mmHg while passing oxygen in an amount of about 0.2 to 0.3% by volume based on the amount of the vapor in the distillation column. Thus, the residue in the still was concentrated to a distillation ratio of 90%, and 110.0 kg of a distillate was obtained. After the distillation, the residue in the still had a viscosity of 12,000 cps at 70° C.

The still residue was divided into six equal portions, and each of the additives shown in Table 1 was added to each of these portions, and each mixture was heated at 70° C. for 15 minutes with stirring. The results are shown in Table 1. It is seen that in Comparative Example 9 in which no additive was used, the residue in the still solidified at room temperature, and on standing, popcorn polymerization was observed.

TABLE 1

| Example (Ex.) or Comparative Example (CEx.) | Additive | Amount of the additive (wt. %) | Viscosity at 70° C. (cps) |
| --- | --- | --- | --- |
| Ex. 7 | Water | 3 | 8 |
| Ex. 8 | Methanol | 10 | 52 |
| Ex. 9 | Salicylic acid | 2 | 32 |
| Ex. 10 | Ethanolamine | 5 | 55 |
| CEx. 8 | n-butanol | 20 | 3200 |
| CEx. 9 | None | 0 | 12000 |

COMPARATIVE EXAMPLE 10

One-fourth of the reaction mixture obtained in Example 7 was subjected to simple distillation without adding any additive. When about 60% of the reaction mixture distilled, the viscosity of the liquid in the still became high, and further distillation failed.

EXAMPLES 11 AND 12 AND COMPARATIVE EXAMPLE 11

The same reactor as used in Example 7 was charged with 100 kg of methacrylic acid, 200 g of p-methoxyphenol and 100 g of phenothiazine, and as a catalyst 3.7 kg of ferric benzoate was added. The reactor was heated to 80° C. While maintaining the inside of the reactor at 80° C., 54 kg of ethylene oxide was added over 3 hours. After the addition of ethylene oxide, the mixture was maintained at 80° C. for 2 hours to complete the reaction. Thereafter, the reaction mixture was cooled to room temperature. The amount of the unreacted methacrylic acid in the reaction product was 0.6% by weight. To the resulting reaction mixture was added 154 g of copper dibutyldithiocarbamate, and the mixture was distilled in the same way as in Example 7. The residue in the still was concentrated to a distillation ratio of 90%, and 137 kg of a distillate was obtained. The residue in the still after the distillation had a viscosity of 86 cps at 70° C. The residue in the still was divided into three equal portions, and each of the additives shown in Table 2 was added to each of these portions. Each mixture was heated at 70° C. for 15 minutes with stirring. The results are shown in Table 2. It is seen that in Comparative Example 11 in which no additive was used, the residue in the still solidified at room temperature, and on standing, popcorn polymerization was observed.

TABLE 2

| | Additive | Amount (wt. %) | Viscosity at 70° C. (cps) |
| --- | --- | --- | --- |
| Example 11 | Acetic acid | 15 | 18 |
| Example 12 | Salicylic acid | 1.7 | 15 |
| Comparative Example 11 | None | 0 | 86 |

EXAMPLE 13

The same reactor as used in Example 7 was charged with 100 kg of acrylic acid, 240 g of p-methoxyphenol and 150 g of copper dibutyldithiocarbamate, and 2.9 kg of ferric acrylate was further added. After sealing the reactor, the reactor was heated. While maintaining the inside of the reactor at 80° C., 84.3 kg of liquid propylene oxide was added over 3 hours. After the addition of propylene oxide, the mixture was maintained further at 80° C. for 2 hours to complete the reaction. The amount of the unreacted acrylic acid in the resulting reaction mixture was 0.8% by weight. To the reaction mixture was added 184 g of copper dibutyldithiocarbamate, and the mixture was distilled in the same way as in Example 7. The residue in the still was concentrated to a distillation ratio of 85%, and 157 kg of a distillate was obtained. The residue in the still after the distillation had a viscosity of 490 cps at 70° C., and solidified at room temperature. Salicylic acid (2% by weight) was added to the residue in the still and the mixture was heated at 70° C. for 15 minutes with stirring. The viscosity of the residue decreased to 81 cps at 70° C.

EXAMPLE 14

Acrylic acid (216 g) was put in a 500 cc three-necked glass flask equipped with a refluxing device and a stirrer, and 0.2 g of copper dibutyldithiocarbamate was added at room temperature with stirring to dissolve it. Furthermore, 7 g of ferric phthalate was added and dissolved with stirring. The solution was heated to 60° C. Then, 158 g of ethylene oxide in gaseous form was blown into the flask over 2.5 hours while cooling the reactor externally with warm water so that the temperature of the reaction system did not exceed 60° C. Ethylene oxide condensed in the refluxing device was not returned to the reaction mixture, but recovered out of the reaction system. The amount of ethylene oxide recovered was 6.5 g. After the blowing of ethylene oxide, the mixture was maintained further at 50° C. for 1 hour to complete the reaction. The amount of the unreacted acrylic acid in the resulting reaction product was 0.6% by weight. To the resulting reaction mixture was added 0.4 g of copper dibutyldithiocarbamate, and the mixture was subjected to simple distillation at about 70° to 80° C. and 3 mmHg while passing about 0.2 to 0.3% by volume, based on the volume of the vapor in the distillation column, of oxygen. The residue in the still was concentrated to a distillation ratio of 90%, and 330 g of a distillate was obtained. After the distillation, the residue in the still had a viscosity of 11000 cps at 70° C., and solidified at room temperature. Water (2% by weight) was added to the residue in the still, and the mixture was heated at 70° C. for 15 minutes. The viscosity of the residue decreased to 20 cps.

EXAMPLE 15-1

A 200-liter reactor (made of SUS 316 stainless steel) equipped with a refluxing device, a thermometer, a heating device, a cooling device and a stirrer was charged with 110 kg of methacrylic acid, 240 g of p-methoxyphenol and 150 g of copper dibutyldithiocarbamate, and they were dissolved. To the resulting solution was added 500 g of iron powder, and the mixture was heated to 110° C. while passing air, thereby dissolving the iron powder. Then, water and 10 kg of methacrylic acid were distilled off from the solution under a reduced pressure of 100 mmHg. The resulting liquid in the reactor had a water content of 0.05% by weight. After sealing the reactor, 54.6 kg of liquid ethylene oxide was added over 3 hours while maintaining the inside of the reactor at 60° C. After the addition of ethylene oxide, the mixture was maintained at 60° C. for 2 hours to complete the reaction. The reaction mixture was cooled to room temperature. The results of the reaction are shown in Table 3.

The individual components of the reaction mixture were analyzed by gas chromatography.

Copper dibutyldithiocarbamate (150 g) was added to the resulting reaction mixture, and the mixture was distilled in a flash distillation device (150 mm in diameter, 1500 mm in height) at about 70° to 80° C. and 3 mmHg while passing oxygen in an amount of about 0.2 to 0.3% by volume based on the amount of the vapor in the distillation column. There was obtained 128 kg of a product having a purity of 99%.

EXAMPLE 15-II

The same reactor as used in Example 15-I was charged with 100 kg of methacrylic acid, 240 g of p-methoxyphenol and 150 g of copper dibutyldithiocarbamate, and they were dissolved. To the resulting solution was added 500 g of iron powder, and the mixture was heated to 110° C. while passing air, thereby dissolving the iron powder. The reaction solution at this time had a water content of 0.24% by weight. After sealing the reactor, 54.6 kg of liquid ethylene oxide was added over 3 hours while maintaining the inside of the reactor at 60° C. After the addition of ethylene oxide, the mixture was further maintained at 60° C. for 17 hours to complete the reaction. The reaction mixture was cooled to room temperature. The results of the reaction are shown in Table 3.

EXAMPLE 16-I

Methacrylic acid (475 g) and 0.4 g of copper dibutyldithiocarbamate were added to a 1-liter autoclave (made of SUS 316 stainless steel) equipped with a stirrer, and 16 g of ferric benzoate was further added and dissolved. The solution was heated, and at 110° C. and 100 mmHg, water and 45 g of methacrylic acid were distilled off from the solution. At this time, the solution had a water content of 0.03% by weight. The inside of the autoclave was purged with nitrogen gas, and the autoclave was sealed up. While maintaining the temperature of the inside of the autoclave at 60° C., 235 g of liquid ethylene oxide was introduced over 3 hours with stirring. After the introduction, the mixture was maintained at the same temperature for 1 hour to complete the reaction. The results of the reaction are shown in Table 3.

EXAMPLE 16-II

The same reactor as used in Example 16-I was charged with 430 g of methacrylic acid and 0.4 g of copper dibutyldithiocarbamate, and 16 g of ferric benzoate was added and dissolved. At this time, the reaction solution had a water content of 0.3% by weight. The inside of the reactor was purged with nitrogen gas, and the reaction solution was heated to 60° C. while maintaining the reactor sealed up. Then, 235 g of liquid ethylene oxide was introduced into the reactor over 3 hours with stirring. After the introduction of ethylene oxide, the mixture was maintained at the same temperature for 15 hours to complete the reaction. The results of the reaction are shown in Table 3.

EXAMPLE 17

The same reactor as used in Example 15-I was charged with 100 kg of methacrylic acid, 240 g of p-methoxyphenol and 150 g of copper dibutyldithiocarbamate, and they were dissolved. To the resulting solution was added 500 g of iron powder, and the mixture was heated to 110° C. while passing air, thereby dissolving the iron powder. Then, 10 kg of benzene was added as an entrainer, and the mixture was heated to 80° C. to distill off water and 10 kg of the added benzene. At this time, the reaction mixture had a water content of 0.02% by weight. After sealing the reactor, liquid ethylene oxide was added while maintaining the inside of the reactor at 60° C. After the addition, the mixture was further maintained at 60° C. for 2 hours to complete the reaction. The resulting reaction mixture was cooled to room temperature. The results of the reaction are shown in Table 3.

TABLE 3

| Example | Reaction time (hours) | Dehydration treatment | Amount of the unreacted methacrylic acid (wt. %) | By-product diester (wt. %) | By-product diethylene glycol monomethacrylate (wt. %) |
|---|---|---|---|---|---|
| 15-I | 5 | Yes | 0.45 | 0.15 | 6.5 |
| 16-I | 4 | Yes | 0.5 | 0.12 | 6.0 |
| 17 | 5 | Yes | 0.4 | 0.11 | 6.5 |
| 15-II | 20 | No | 0.9 | 0.25 | 7.5 |
| 16-II | 18 | No | 1.0 | 0.21 | 7.0 |

EXAMPLE 18

Methacrylic acid (480 g) and 0.4 g of copper dibutyldithiocarbamate were charged into the same reactor as used in Example 16-I, and dissolved. To the resulting solution was added 21.5 g of iron powder, and the mixture was heated to 110° C. while passing air, thereby dissolving the iron powder. Then, at 100 mmHg, water and 50 g of the methacrylic acid were distilled off from the solution. At this time, the solution had a water content of 0.04% by weight. The inside of the reactor was purged with nitrogen, and the reactor was sealed up. While maintaining the inside of the reactor at 80° C., 305 g of liquid propylene oxide was introduced over 3 hours with stirring. After the introduction of the propylene oxide, the mixture was maintained at 80° C. for 2 hours to complete the reaction. The resulting reaction mixture was found to contain 0.7% by weight of the unreacted methacrylic acid, 0.2% by weight of the by-product diester, and 8.5% by weight of the by-product dipropylene glycol monomethacrylate.

What we claim is:

1. In a process for producing 2-hydroxyalkyl acrylate or methacrylate ester monomer by esterifying acrylic acid or methacrylic acid with an alkylene oxide having 2 to 4 carbon atoms in the presence of an esterification catalyst and distilling the resulting reaction mixture in a distillation column in which the ester monomer is vaporized, and a distillation residue is formed, the improvement comprising
   superheating the vapor of the ester monomer from the distillation column,
   providing a condenser of the gas-liquid direct contact type having a gas inlet portion,
   maintaining the inner wall of the gas inlet portion at a temperature below the boiling point of the ester monomer at the operating pressure within said condenser,
   introducing the superheated vapor of the ester monomer into the condenser through said gas inlet portion,
   spraying said condenser, in the direction of, and in contact with said superheated vapor of the ester monomer introduced into the condenser, with a liquid of said ester monomer, at a temperature below the boiling point of said ester monomer at said operating pressure whereby said vapor is condensed to a liquid at said temperature below the boiling point of said ester monomer at said operating pressure.

2. The process of claim 1 wherein the esterification catalyst is at least one ferric salt of a carboxylic acid selected from the group consisting of acrylic acid, methacrylic acid, benzoic acid, phthalic acids and salicylic acid.

3. The process of claim 1 wherein during the distillation, salicylic acid is caused to be present in the reaction mixture in the distillation column.

4. The process of claim 3 wherein the salicylic acid is added to the reaction mixture in an amount of from 0.05 to 10% by weight, based on the reaction mixture before distillation.

5. The process of claim 3 wherein during the distillation, at least one copper salt of a dialkyldithiocarbamic acid with the alkyl group having 1 to 4 carbon atoms is caused to be present in the reaction mixture in the distillation column.

6. The process of claim 2 or 5 wherein after the distillation, at least one compound selected from the group consisting of water, acetic acid, salicylic acid, ethanolamines and methanol is added to the distillation residue to stabilize the residue.

7. The process of claim 6 wherein the added compound is water.

8. The process of claim 6 wherein the added compound is acetic acid.

9. The process of claim 6 wherein the added compound is salicylic acid.

10. The process of claim 6 wherein the added compound is ethanolamines.

11. The process of claim 6 wherein the added compound is methanol.

12. The process of claim 6 wherein the amount of the compound added to the distillation residue is from 0.5 to 30% by weight based on the distillation residue.

13. The process of claim 1 wherein a solution obtained by dissolving a ferric salt of a carboxylic acid in acrylic or methacrylic acid is dehydrated and used in the esterification reaction.

14. The process of claim 1 wherein a solution of a ferric salt in acrylic or methacrylic acid obtained by dissolving iron powder in acrylic or methacrylic acid in the presence of a copper, potassium or sodium salt of a dialkyldithiocarbamic acid having an alkyl group with 1 to 4 carbon atoms while passing molecular oxygen through the solution is used in the esterification reaction.

15. The process of claim 14 wherein the ferric salt solution is dehydrated before using it in the esterification reaction.

16. The process of claim 1 wherein the inner wall of the gas inlet portion is maintained at a temperature of from 20° C. below the boiling point of the ester monomer to room temperature and the liquid of the ester monomer is sprayed into the condenser at a temperature of from 20° C. below the boiling point of the ester monomer to room temperature.

17. The method of claim 1 wherein the liquid of the ester monomer is sprayed in an amount of from 10 to 200 times the weight of the superheated vapor of the ester monomer.

* * * * *